(12) United States Patent
Meridew

(10) Patent No.: US 8,641,718 B2
(45) Date of Patent: Feb. 4, 2014

(54) METHOD AND APPARATUS FOR HARVESTING CARTILAGE FOR TREATMENT OF A CARTILAGE DEFECT

(75) Inventor: Jason D. Meridew, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 642 days.

(21) Appl. No.: 12/907,610

(22) Filed: Oct. 19, 2010

(65) Prior Publication Data
US 2012/0095469 A1 Apr. 19, 2012

(51) Int. Cl.
*A61F 2/46* (2006.01)

(52) U.S. Cl.
USPC ........................................................ 606/86 R

(58) Field of Classification Search
USPC ........ 623/16.11, 23.61, 23.63, 23.72; 606/80, 606/86 R
See application file for complete search history.

(56) References Cited

U.S. PATENT DOCUMENTS

| | | |
|---|---|---|
| 493,730 A | 3/1893 | MacKenzie |
| 1,848,590 A | 3/1932 | Willis |
| 1,911,873 A | 5/1933 | Balton |
| 2,062,257 A | 11/1936 | Douglas et al. |
| 2,573,462 A | 10/1951 | Lindsey |
| 2,591,516 A | 4/1952 | Darnell |
| 2,754,864 A | 7/1956 | Elsy |
| 2,779,361 A | 1/1957 | McKiff |
| 3,430,526 A | 3/1969 | Valenziano |
| 3,609,056 A | 9/1971 | Hougen |
| 3,848,601 A | 11/1974 | Ma et al. |
| 4,007,732 A | 2/1977 | Kvavle et al. |
| 4,010,737 A | 3/1977 | Vilaghy et al. |
| 4,059,115 A | 11/1977 | Jumashev et al. |
| 4,177,797 A | 12/1979 | Baylis et al. |
| 4,596,243 A | 6/1986 | Bray |
| 4,649,918 A | 3/1987 | Pegg et al. |
| 4,741,651 A | 5/1988 | Despres |
| 4,772,286 A | 9/1988 | Goble et al. |
| 4,779,689 A | 10/1988 | Paxton, III |
| 4,782,833 A | 11/1988 | Einhorn et al. |
| 4,830,000 A | 5/1989 | Shutt |
| 4,856,693 A | 8/1989 | Kageyama et al. |
| 4,862,882 A | 9/1989 | Venturi et al. |
| 4,865,146 A | 9/1989 | Ohe |

(Continued)

FOREIGN PATENT DOCUMENTS

| | | |
|---|---|---|
| DE | 19503504 A1 | 3/1996 |
| EP | 0495487 A2 | 7/1992 |
| WO | WO-9106246 | 5/1991 |

OTHER PUBLICATIONS

"Bone Dowel Harvester", Arthrotek, Inc., (2003).

(Continued)

*Primary Examiner* — Anu Ramana
(74) *Attorney, Agent, or Firm* — Harness, Dickey

(57) ABSTRACT

A method for treating a cartilage defect can include identifying an area of excessive boney growth on at least one of a femoral head and a femoral neck of a patient where the excessive boney growth area is covered with articular cartilage. A portion of the articular cartilage can be harvested from the identified area of excessive boney growth and an area of cartilage damage in an acetabulum of the patient can be identified. The harvested portion of the articular cartilage can be implanted into the identified area of cartilage damage in the acetabulum.

19 Claims, 7 Drawing Sheets

(56) References Cited

U.S. PATENT DOCUMENTS

| | | | |
|---|---|---|---|
| 4,895,146 A | 1/1990 | Draenert |
| 4,901,711 A | 2/1990 | Goble et al. |
| 4,913,143 A | 4/1990 | Oloff et al. |
| 4,927,421 A | 5/1990 | Goble et al. |
| 4,936,313 A | 6/1990 | Burkhardt et al. |
| 4,950,270 A | 8/1990 | Bowman et al. |
| 4,985,032 A | 1/1991 | Goble |
| 4,997,434 A | 3/1991 | Seedhom et al. |
| 5,037,426 A | 8/1991 | Goble et al. |
| 5,082,403 A | 1/1992 | Sutton et al. |
| 5,127,920 A | 7/1992 | MacArthur |
| 5,129,902 A | 7/1992 | Goble et al. |
| 5,139,499 A | 8/1992 | Small et al. |
| 5,139,520 A | 8/1992 | Rosenberg |
| 5,147,362 A | 9/1992 | Goble |
| 5,152,763 A | 10/1992 | Johnson |
| 5,190,548 A | 3/1993 | Davis |
| 5,197,967 A | 3/1993 | Wilson |
| 5,205,685 A | 4/1993 | Herbert |
| 5,211,647 A | 5/1993 | Schmieding |
| 5,257,996 A | 11/1993 | McGuire |
| 5,269,786 A | 12/1993 | Morgan |
| 5,320,115 A | 6/1994 | Kenna |
| 5,320,626 A | 6/1994 | Schmieding |
| 5,341,816 A | 8/1994 | Allen |
| 5,391,170 A | 2/1995 | McGuire et al. |
| 5,397,357 A | 3/1995 | Schmieding et al. |
| 5,415,651 A | 5/1995 | Schmieding |
| 5,423,823 A | 6/1995 | Schmieding |
| 5,496,326 A | 3/1996 | Johnson |
| 5,520,693 A | 5/1996 | McGuire et al. |
| 5,562,669 A | 10/1996 | McGuire |
| 5,591,170 A | 1/1997 | Spievack et al. |
| 5,603,716 A | 2/1997 | Morgan et al. |
| 5,632,747 A | 5/1997 | Scarborough et al. |
| 5,697,935 A | 12/1997 | Moran et al. |
| 5,772,664 A | 6/1998 | DeSatnick et al. |
| 5,782,835 A | 7/1998 | Hart et al. |
| 5,785,714 A | 7/1998 | Morgan et al. |
| 5,803,678 A | 9/1998 | Korb et al. |
| 5,865,834 A | 2/1999 | McGuire |
| 5,918,604 A | 7/1999 | Whelan |
| 5,919,196 A | 7/1999 | Bobic et al. |
| 5,928,238 A | 7/1999 | Scarborough et al. |
| 6,017,348 A | 1/2000 | Hart et al. |
| 6,110,178 A | 8/2000 | Zech et al. |
| 6,110,209 A | 8/2000 | Stone |
| 6,146,385 A | 11/2000 | Torrie et al. |
| 6,369,295 B1* | 4/2002 | Cheah et al. ............. 800/18 |
| 6,451,023 B1 | 9/2002 | Salazar et al. |
| 6,530,928 B1 | 3/2003 | Frei et al. |
| 6,588,992 B2 | 7/2003 | Rudolph |
| 6,591,581 B2 | 7/2003 | Schmieding |
| 6,592,588 B1 | 7/2003 | Bobic et al. |
| 6,808,182 B2 | 10/2004 | Lin |
| 6,857,830 B2 | 2/2005 | Holcomb |
| 7,427,293 B2 | 9/2008 | Nycz et al. |
| 8,162,967 B1 | 4/2012 | Kaiser et al. |
| 2002/0032447 A1 | 3/2002 | Weikel et al. |
| 2002/0099382 A1 | 7/2002 | Salazar et al. |
| 2002/0099383 A1 | 7/2002 | Salazar et al. |
| 2002/0111632 A1 | 8/2002 | Lechot |
| 2002/0157676 A1 | 10/2002 | Schmieding |
| 2002/0188353 A1 | 12/2002 | Philippon |
| 2002/0193802 A1 | 12/2002 | Zdeblick et al. |
| 2003/0055431 A1 | 3/2003 | Brannon |
| 2004/0034437 A1 | 2/2004 | Schmieding |
| 2005/0137600 A1* | 6/2005 | Jacobs et al. ............. 606/79 |
| 2007/0260256 A1 | 11/2007 | Beaule |
| 2007/0270711 A1 | 11/2007 | Gil et al. |
| 2007/0276506 A1* | 11/2007 | Troxel .................. 623/23.63 |
| 2008/0195221 A1 | 8/2008 | Howald et al. |
| 2008/0249632 A1* | 10/2008 | Stone et al. ............. 623/23.5 |
| 2008/0306608 A1 | 12/2008 | Nycz et al. |
| 2009/0060974 A1 | 3/2009 | Schmieding et al. |

OTHER PUBLICATIONS

"Prestige Cervical Disc System Surgical Technique", 12 pgs.

"Techniques for ACL Reconstruction with Multi-Trac™ Drill Guide," available by 2000.

Acufex Microsurgical, Inc., "Endoscopic Technique for ACL Reconstruction with Pro-Trac Tibial Guide: Endobutton Fixation," available by 2000.

Arthrex, Osteochondral Autograft Transfer System (OATS), "Surgical Technique," Arthrex, Inc. (1998) 25 pages.

Arthrotek, Inc., Autogenous Bone Coring: A Scientific Approach, 2004.

Arthrotek® OCD System, Osteochondral Defect Surgical Technique, brochure, 1999 (4 pages).

Bobic, V., "An Update on Arthroscopic Osteochondral Autograft Transplantation in ACL Reconstrction," AOSSM 22nd Annual Meeting, (Jun. 1996).

Bobic, V., "Arthroscopic Osteochondral Autograft Transplantation in Anterior Cruciate Ligament Reconstruction: A Preliminary Clinical Study," J Bone Joint Surgery >BR!, vol. 78-B: Supp. 1 (Mar. 1996).

Bobic,, V., "Arthroscopic Osteochondral Autograft Transplantation in Chronic Anterior Cruciate Ligament Reconstruction," Knee Surg. Sports Traumatol, Arthros (May 1996) 3:262-264.

Brittberg, M. et al., "Treatment of Deep Cartilage Defects in the Knee with Autologous Chondrocyte Transplantation," New England J. Med., vol. 331, No. 14, pp. 889-895 (Oct. 6, 1994).

Buckwalter, J., "Solution for a New Methods of Treating Chondral Defects in the Knee" (undated).

Christel, P., et al., "Osteochondral Grafting Using The Mosaicplasty Technique," www.maitrise-orthop.com/corpusmaitri/orthopaedic/mo76_mosaicplasty/index.shtml (23 pages) Printed Mar. 23, 2005.

Fabbriciani, C. et al., "Osteochondral Autograft in the Treatment of O.D. of the Knee," Orthopaedic Clinic, Catholic Univ., Rome, Italy (1996).

Garrett; John C., "Osteochondritis Dissecans"; Clinics in Sports Medicine; vol. 10, No. 3; (Jul. 1991); pp. 569-593.

Hangody, Laszlo, et al., "MosaicPlasty™ Osteochondral Grafting Technique Guide", Smith & Nephew Endoscopy, (Jul. 1996).

Innovasive COR.TM. System, Innovasive Devices, Inc., Jan. 1997.

Innovasive COR.TM. System: An Arthroscopic Technique for Harvesting and Transplanting Bone Grafts, Innovasive Devices, Inc., pp. 1-4, Sep. 1996.

Innovasive Cor™ System, Innovasive Devices, Inc. (Jan. 1997) pp. 1-2.

Instrument Makar, Inc., "Bone Grafters Surgical Technique," Dec. 1995.

Instrument Makar, Inc.,"New Directions in Arthroscopic Innovation," 1991 Catalogue.

L. Hangody, "Autologous osteochondral mosaic-like graft technique for replacing weight-bearing cartilage defects," ESSKA 96, Budapest, Hungary (May 10-15, 1996).

Malinin, M.D. et al., Articular Cartilage Nutrition is Mediated by Subchondral Bone: A Long-Term Autograft Study in Baboons; Osteoarthritis and Cartilage, Journal of the Osteo Arthritis Research Society International, (2000) vol. 8, No. 6, pp. 483-491.

Malinin, T., M.D., Human Cadaver Femoral Head Homografts for Anterior Cervical Spine Fusions, Reprinted from Surgical Neurology, vol. 7, No. 4, Apr. 1977.

Malinin, T.I., "University of Miami Tissue Bank: Collection of Postmortem Tissues for Clinical Use and Laboratory Investigation", From the Departments of Surgery and Pathology, University of Miami School of Medicine and the Veterans Administration Hospital, Transplantation Proceedings, vol. VIII, No. 2, Supplement 1 Jun. 1976 (pp. 53-58).

Malinn, M.D., et al, "Hypothermic Storage and Cryopreservation of Cartilage, An Experimental Study," No. 197 (Jul.-Aug. 1985).

Mankin et al., Restoration of the Osteoarthrotic Joint, J Bone Joint Surgery, vol. 78-A, No. 1, pp. 1-2 (Jan. 1996).

Matsusue, Y., "Arthroscopic Multiple Osteochondral Transplantation to the Chondral Defect in the Knee Associated with Anterior Cruciate Ligament Disruption," Arthroscopy: The Journal of Arhtroscopic and Related Surgery 9(3), pp. 318-321 (Jun. 1993).

(56) References Cited

OTHER PUBLICATIONS

N. Gould, "Trephining Your Way," Orthopedic Clinics of North America, vol. 4, No. 1, pp. 157-164 (Jan. 1973).

Outerbridge, H.K., et al; "The Use of a Lateral Patellar Autologous Graft for the Repair of a Large Osteochondral Defect in the Knee"; The Journal of Bone and Joint Surgery; vol. 77-A, No. 1; (Jan. 1995); pp. 65-72.

van Dyk, G.E., et al; "Cancellous Bone Grafting of Large Osteochondral Defects: An Experimental Study in Dogs"; Arthroscopy: The Journal of Arthroscopic and Related Surgery; vol. 14, No. 3; (Apr. 1998); pp. 311-320.

Yamashita, F., "The Transplantation of an Autogeneic Osteochondral Fragment for Osteochondrtis Dissecans of the Knee," Clinical Orthopaedics, No. 201, pp. 43-50 (Dec. 1985).

\* cited by examiner

… (1)

METHOD AND APPARATUS FOR HARVESTING CARTILAGE FOR TREATMENT OF A CARTILAGE DEFECT

FIELD

The present teachings relate generally to a method for harvesting cartilage for treatment of a cartilage defect and, more particularly, to a method of harvesting cartilage for treatment of a cartilage defect site in one of an acetabulum or a femoral head.

BACKGROUND

The statements in this section merely provide background information related to the present disclosure and may not constitute prior art.

In an anatomy, such as a human anatomy, various portions of the body are interconnected through soft tissues. For example, ligaments and cartilage interconnect various portions of the anatomy to provide selected articulations of adjacent bone portions. Over time, the cartilage may become weakened or damaged due to various reasons including injury, fatigue, age, disease, etc. and may need to be repaired or replaced.

A cartilage autograft or allograft can be used to repair or replace the damaged cartilage. When an autograft is used to repair the damaged cartilage, the autograft is typically obtained from another area or portion of the anatomy where the cartilage is healthy and may be under less strain, but may still be utilized in connection with the articulation of an associated anatomical joint.

While these conventional cartilage autograft techniques work for their intended purpose, there nevertheless exists a need in the art for an improved autograft technique for treating a cartilage defect.

SUMMARY

This section provides a general summary of the disclosure, and is not a comprehensive disclosure of its full scope or all of its features.

According to one exemplary aspect of the present teachings, a method for treating a cartilage defect can include identifying an area of excessive boney growth on at least one of a femoral head and a femoral neck of a patient where the excessive boney growth area is covered with articular cartilage. A portion of the articular cartilage can be harvested from the identified area of excessive boney growth and an area of cartilage damage in an acetabulum of the patient can be identified. The harvested portion of the articular cartilage can be implanted into the identified area of cartilage damage in the acetabulum.

According to another exemplary aspect of the present teachings, a method for treating a cartilage defect can include identifying an area of excessive boney growth on at least a portion of one of a femoral head and a femoral neck of a patient where the excessive boney growth area is covered with articular cartilage. At least one cartilage plug can be harvested from only the identified area of excessive boney growth where the at least one cartilage plug includes an articular cartilage layer and an underlying bone layer. The method can further include identifying a cartilage defect site having an area of cartilage damage in at least one of the acetabulum and the femoral head of the patient and preparing the identified cartilage defect site for receipt of the at least one harvested cartilage plug. The preparation can include forming a closed end bore through the respective area of cartilage damage, where the closed end bore can have a width greater than a determined width of the area of cartilage damage. The at least one harvested cartilage plug can be implanted into the formed closed end bore of the at least one prepared defect site such that the implanted cartilage plug is received in the closed end bore in an interference fit configuration. The remaining excessive boney growth can be removed from the at least one of the femoral head and femoral neck after harvesting the at least one cartilage plug.

Further areas of applicability will become apparent from the description provided herein. It should be understood that the description and specific examples are intended for purposes of illustration only and are not intended to limit the scope of the present teachings.

DRAWINGS

The present teachings will become more fully understood from the detailed description, the appended claims and the following drawings. The drawings are for illustrative purposes only and are not intended to limit the scope of the present teachings.

DETAILED DESCRIPTION

Figure 1:
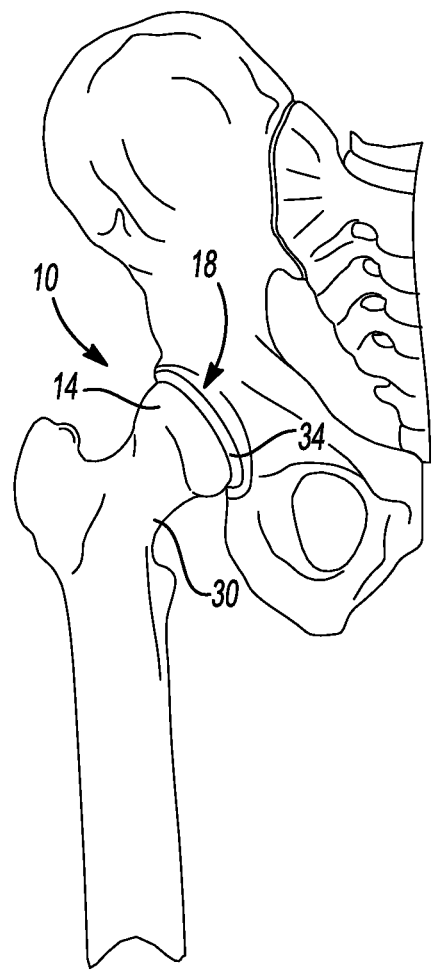
FIG. 1 is a perspective view of a hip joint according to the present teachings.

The following description is merely exemplary in nature and is not intended to limit the present disclosure, its application, or uses. It should be understood that throughout the drawings, corresponding reference numerals indicate like or corresponding parts and features.

Figure 2:
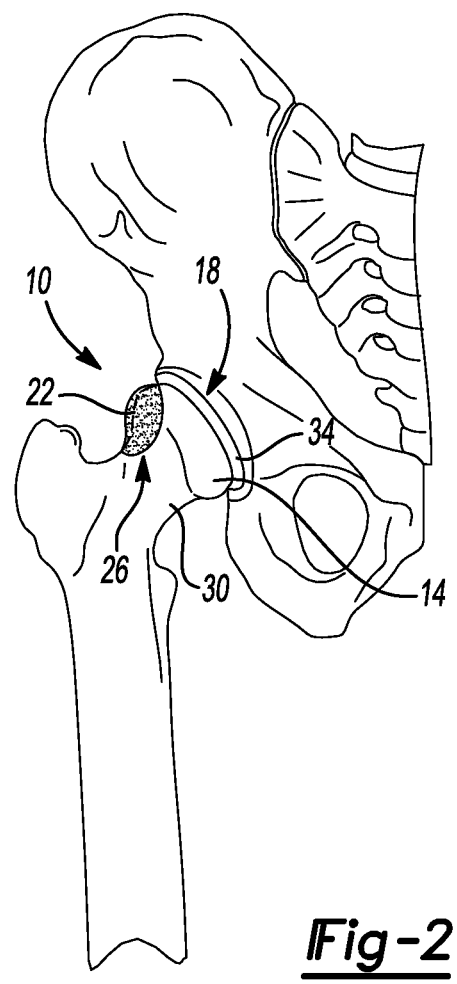
FIG. 2 is a perspective view of a hip joint with an excessive growth or build-up on the femoral neck and femoral head according to the present teachings.
Figure 3:
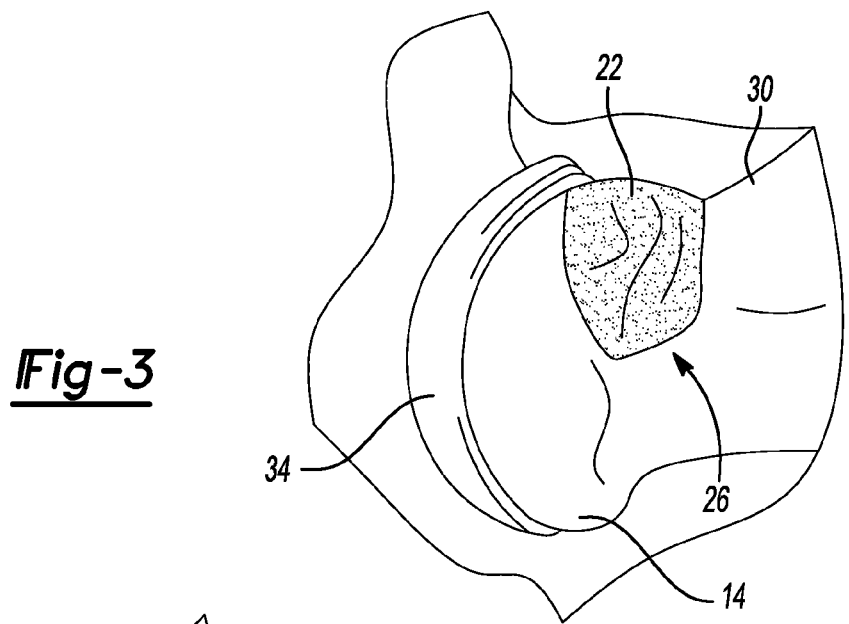
FIG. 3 is a perspective view illustrating a femoro-acetabular impingement condition according to the present teachings.
Figure 4:
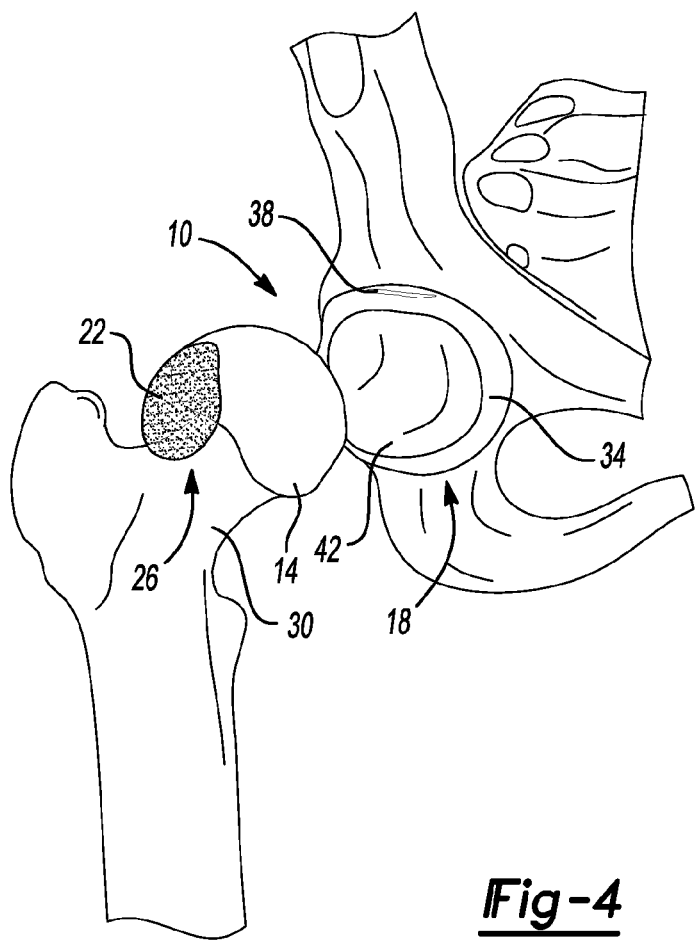
FIG. 4 is a perspective view illustrating a labral tear in a rim of the acetabulum according to the present teachings.

Referring now to FIGS. 1-11 of the drawings, various methods are disclosed according to the present teachings for treating a cartilage defect associated with a hip joint of the anatomy. With particular reference to FIGS. 1-4, an exemplary hip joint 10 is shown where the femoral head 14 is seated in the acetabulum 18 for articulation thereabout, as shown in FIG. 1. In certain circumstances, an abnormal or excessive boney growth area or build-up 22 can occur in a region 26 along the femoral head 14 and femoral neck 30, as generally shown in FIG. 2. The boney growth area 22 can result in an impingement condition generally known as femoro-acetabular impingement (FAI) where the boney growth area 22 impinges on the acetabular rim surrounding the acetabulum 18 when the femoral head 14 articulates relative thereto, as generally shown in FIGS. 3 and 4. Such impingement can result in damage to the labrum 34, such as a labral tear 38, as well as damage over time to articular cartilage 42 of the acetabulum 18. As a result, it can be desirable to remove the boney growth area 22 by way of burrs, milling or osteotomes.

With additional reference to FIGS. 5-11, a method for treating a cartilage defect in the hip joint 10, including harvesting cartilage from the boney growth area 22, will now be described in greater detail. The method can include identifying the boney growth area 22 in the region 26 extending about the femoral neck 30 and femoral head 14. The boney growth area 22 can be covered with articular cartilage 54 that also covers the femoral head 14, as shown for example in FIG. 5. The boney growth area 22 and articular cartilage 54 associated therewith can be inspected to determine, for example, if there has been any damage to the cartilage 54 as a result of FAI associated with the boney growth area 22.

Figure 6:
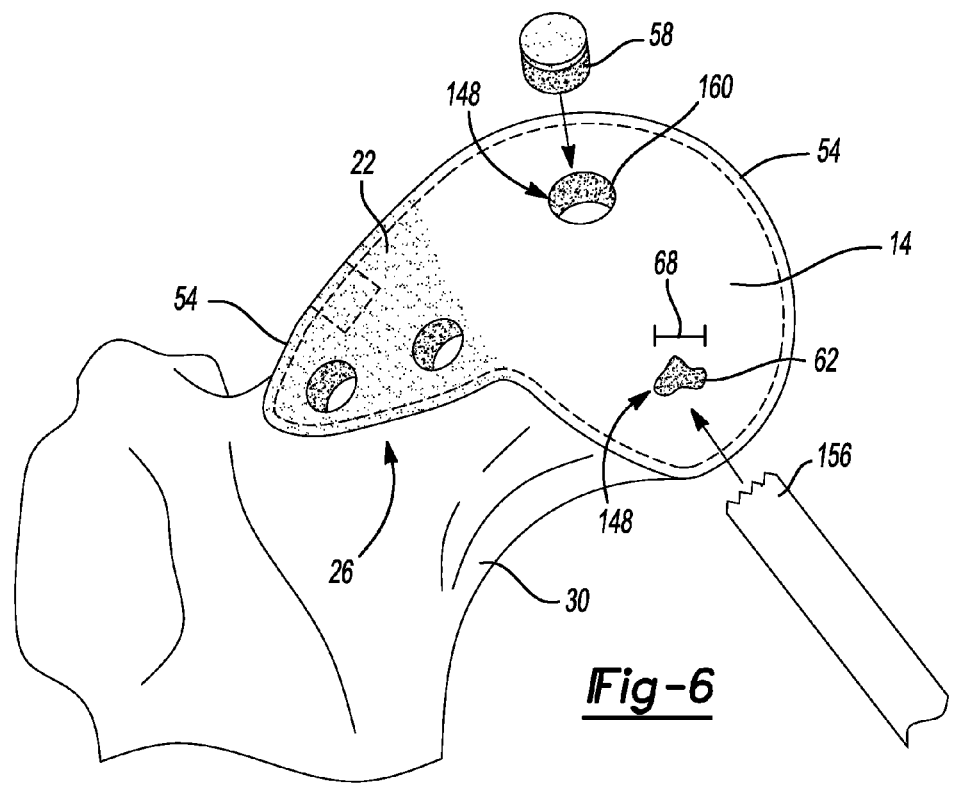
FIG. 6 is another perspective view of the cartilage plug harvesting technique associated with the femoral head according to the present teachings.
Figure 7:
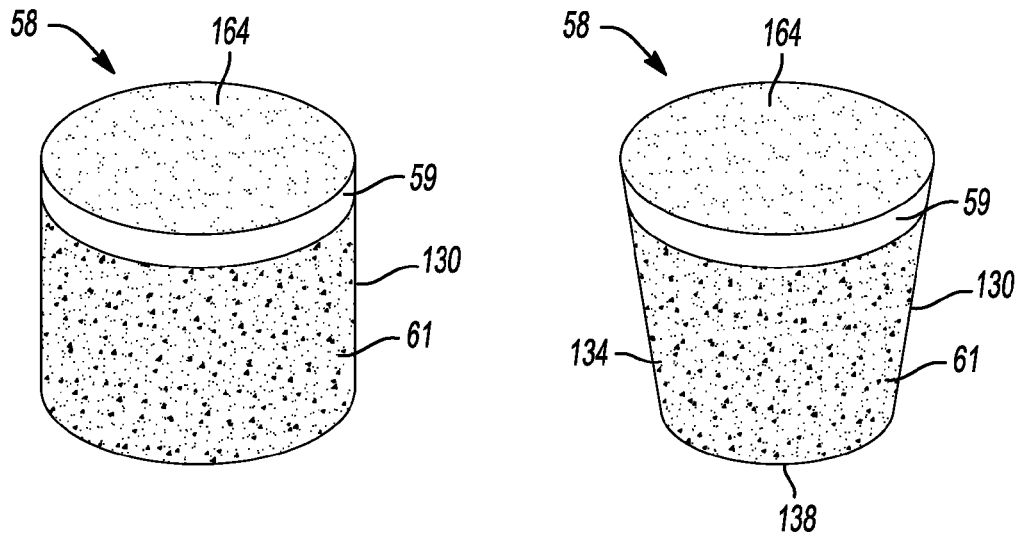
FIG. 7 is a perspective view of exemplary harvested cartilage plugs according to the present teachings.
Figure 9:
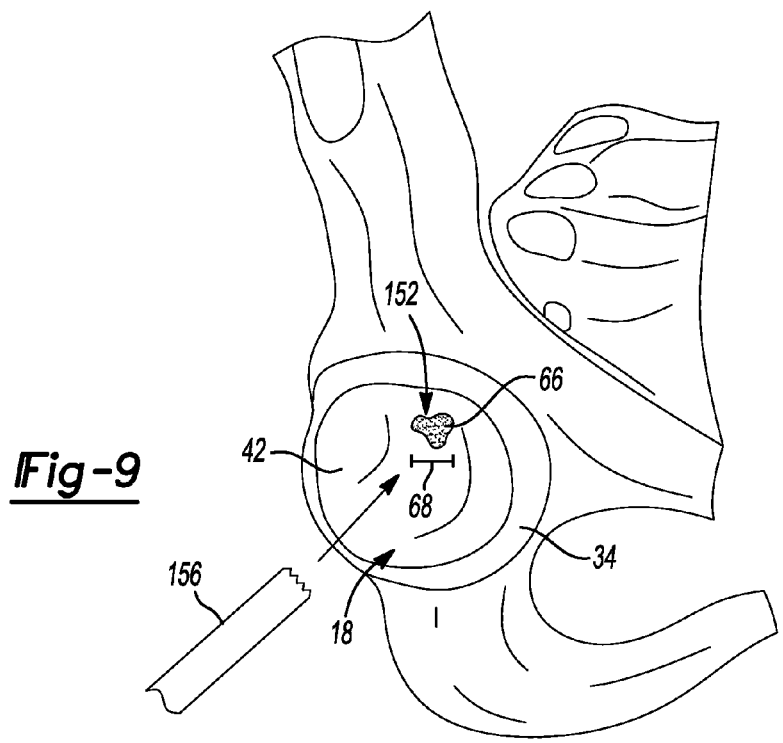
FIG. 9 is a perspective view of the cartilage plug harvesting technique associated with the acetabulum according to the present teachings.

Once it has been determined that the articular cartilage 54, or a specific area thereof, is suitable for harvesting, preparations can be made to harvest a cartilage core or plug 58 from the boney growth area 22. As will be described in greater detail below, the cartilage plug 58 can include an articular cartilage layer 59 and a bone layer 61 harvested from the respective articular cartilage layer 54 and underlying bone of the boney growth area 22, as generally shown in FIGS. 6 and 7. In one aspect of the present teachings, the cartilage plug 58 can be harvested from only the excessive boney growth area 22. The preparations can include identifying a cartilage defect 62 in the femoral head 14 and/or a cartilage defect 66 in the acetabulum 18, as generally shown in FIGS. 6 and 9, respectively. It should be appreciated that the harvested cartilage plug 58 could be also used to treat various cartilage defects that may not necessarily be limited to the femoral head 14 or acetabulum 18. Once the cartilage defect 62 and/or 66 has been identified, a size of the defect can be determined, such as a width 68 of the defect, for use in determining an appropriate instrument size for harvesting the cartilage plug 58 with an appropriate size to treat the identified cartilage defect 62, 66.

With additional reference to FIGS. 12A-13B, the cartilage plug 58 can be harvested from the boney growth area 22 with any appropriate instrument suitable for such harvesting, such as the exemplary harvesting instrument described in commonly owned pending U.S. application Ser. No. 10/687,108, the entirety of which is hereby incorporated by reference herein. The exemplary harvesting instrument can include a harvesting member 74 generally defining a sharpened or coring end portion 78 suitable for engaging the anatomy and an opposite end 82 configured for engagement with a handle or other suitable device capable of being driven with a mallet or the like. The harvesting member 74 can include a generally elongated body 84 extending between the end portion 78 and opposite end 82 and can be formed of a suitable material so as to define an inner cannula 86. The inner cannula 86 can allow the cartilage plug 58 or material to be harvested to be received therein.

The coring end 78 can be tapered and include a sharpened or cutting edge 90. The cutting edge 90 can be used to cut into a selected portion of the anatomy, such as the articular cartilage 54 and underlying bone of the boney growth area 22. In addition, the harvesting member 74 can include demarcations 94 on an outer surface 98 thereof that can be used to indicate or select a length or depth of a core portion, such as cartilage plug 58. A user may view the demarcations 94 on the exterior of the harvesting member 74 to determine the depth of the harvesting member 74 within the boney growth area 22. It will be understood that the harvesting member 74 may be formed of any appropriate material. For example, various biocompatible metals may be used that may be easily formed and sharpened to form the sharpened edge 90 and inner cannula 86, where such materials can include biocompatible metals, ceramics and polymers.

Figure 13B:
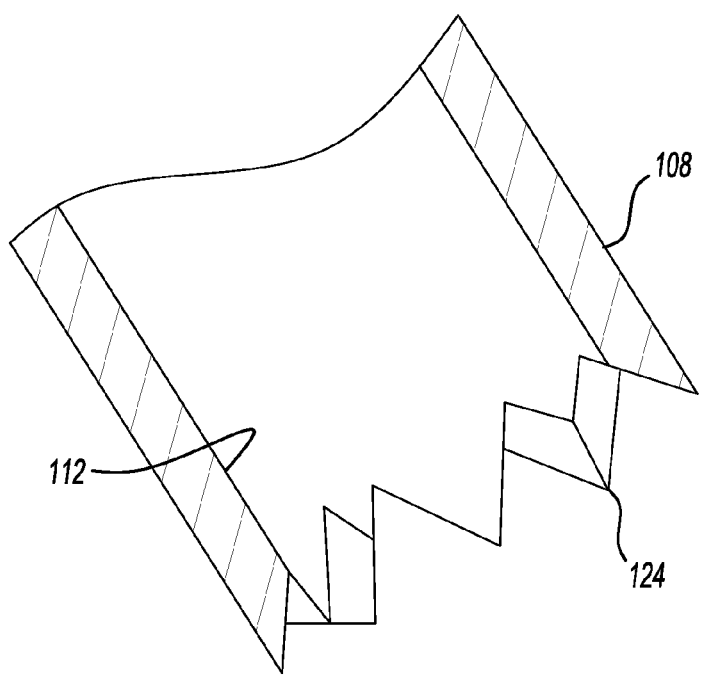
FIGS. 13A and 13B are views of an alternative exemplary harvesting instrument according to the present teachings.
Figure 12A:
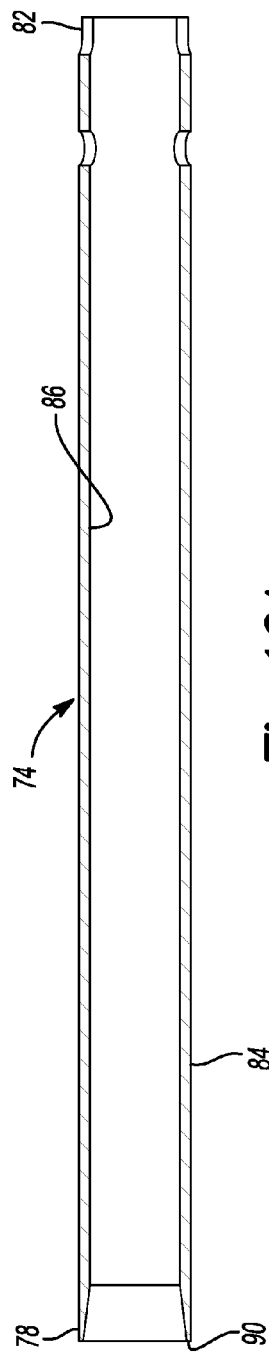
FIGS. 12A and 12B are views of an exemplary harvesting instrument according to the present teachings.
Figure 12B:
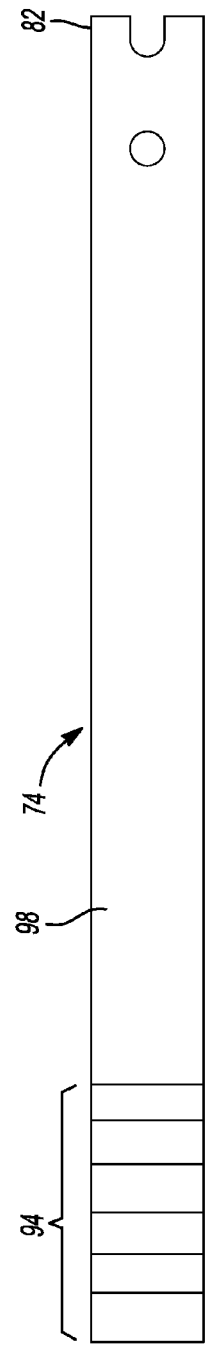
Figure 13A:
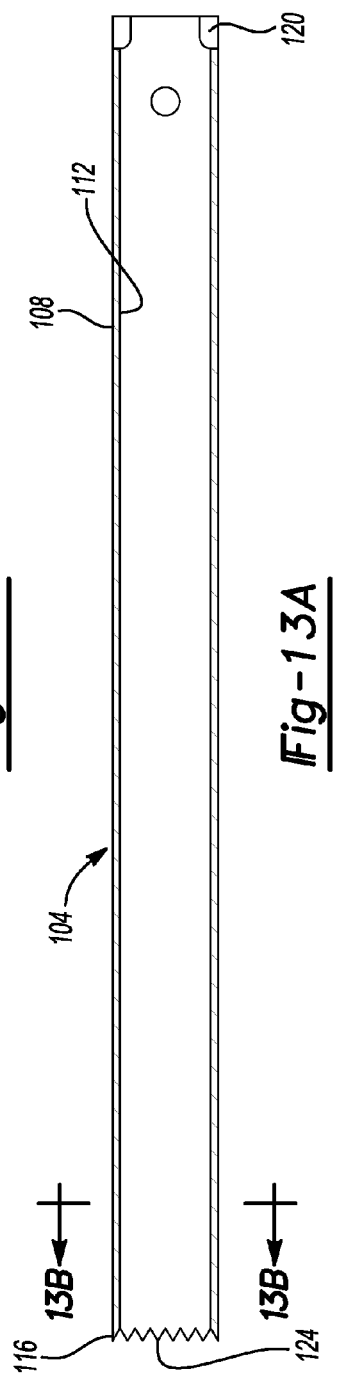

With particular reference to FIGS. 13A and 13B, an alternative harvesting member 104 is illustrated according to the present teachings. Harvesting member 104 can also include an elongated body 108 that defines an inner cannula 112. The body 108 can include a cutting portion 116 at one end and a tool engaging portion 120 at an opposite end. The tool engaging portion 120 can be coupled to an appropriate tool (not shown) to rotate or drive the harvesting member such that the cutting portion 116 can harvest the cartilage plug 58, as will be described in greater detail herein. The cutting portion 116 can define a plurality of cutting teeth 124, as shown for example in FIG. 13B. The cutting teeth 124 can be defined in any appropriate manner such that they can be rotated to harvest a selected portion of the articular cartilage 54 and underlying bone of the boney growth area 22, such as cartilage plug 58. The harvested cartilage plug can be collected within the inner cannula 112. It will be understood that demarcations, such as demarcations 94, can also be included on an outer surface of harvesting member 104.

Figure 5:
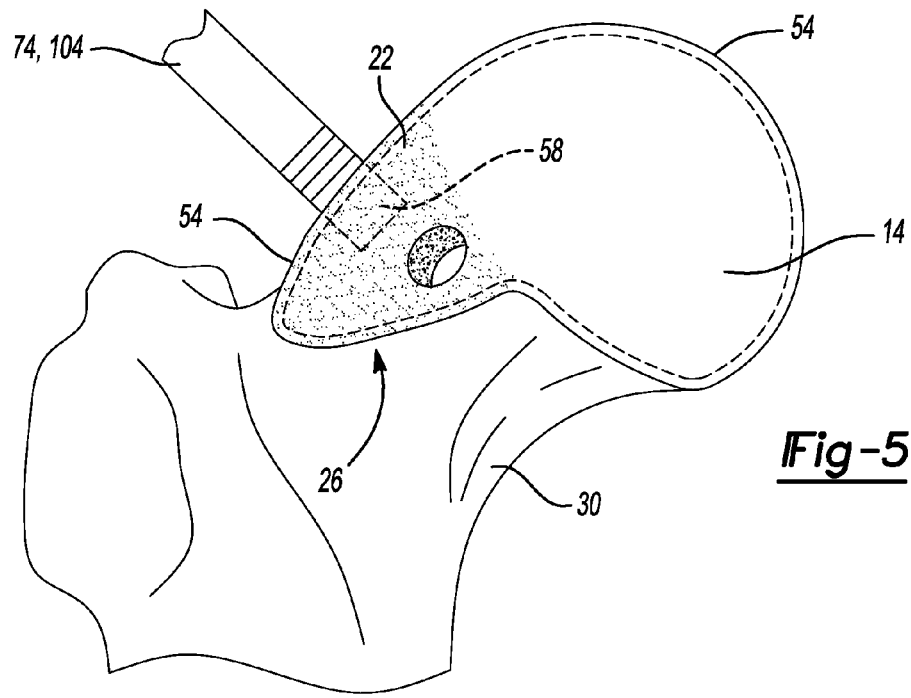
FIG. 5 is a perspective view of a cartilage plug harvesting technique according to the present teachings.

Returning back to FIGS. 5-11, one of the harvesting members 74 or 104 can be used to harvest the cartilage plug 58 from the boney growth area 22, as generally shown in FIG. 5. If the harvesting member 74 is used, member 74 can be coupled to a handle and driven with a mallet or the like into the boney growth area 22 to a desired depth indicated by demarcations 94, as shown in FIG. 5. After the harvesting member 74 has reached the desired depth, the harvesting member can be loosed or removed from the boney growth area 22 by rotating the harvesting member 74. The rotation can break off a core portion or cartilage plug 58 that is positioned within the inner cannula 86 defined by the harvesting member 74. On the other hand, if harvesting member 104 is used, member 104 can be coupled to a tool for rotating the cutting teeth 124 such that the harvesting member can cut into the boney growth area 22 to the desired depth indicated by demarcations 94 and harvest the cartilage plug 58.

Depending on the size of the boney growth area 22, one or more cartilage plugs 58 can be harvested therefrom. For example, three or more cartilage plugs 58 can be harvested from various portions of the boney growth area 22, as generally shown in FIG. 5. The harvested cartilage plugs 58 can include a cylindrical shape or form 130 having various diameters, such as a diameter of 5 mm, which may be required to treat a similarly sized defect area in the femoral head 14 and/or acetabulum 18, as generally shown in FIG. 7. It should be understood that cartilage plugs of various sizes and numbers can be harvested from the boney growth area 22 as may be required to treat a cartilage defect or defects of various sizes. In this manner, an overall size, shape and/or depth of the abnormal excessive boney growth area 22 that would need to be removed to return the femoral head 14 and/or neck 30 to the natural shape can be determined. Once this has been determined, various different sizes of cartilage plugs 58 can be harvested from specific areas of the excessive boney growth area 22 that is to be removed so as to optimize or maximize the amount of plugs that can be harvested. For example, if various cartilage defect sites have been identified that include both shallow and deep depths, then cartilage plugs 58 having shallow depths can be harvested from shallower areas of the excessive boney growth area 22 so as to save deeper areas of the excessive boney growth area 22 for cartilage plugs that require a greater depth.

In addition, while the cartilage plug 58 has been described as having a generally cylindrical form 130, it should be appreciated that the defect can be harvested in various shapes including a generally conical shape 134, as also shown in FIG. 7. The conical shape 134 can have a larger width or diameter at the articular cartilage layer 59 and a smaller diameter at the end 138 of the underlying bone layer 61. Other possible shapes include square, rectangular or triangular in cross-section. The shapes could be formed, for example, with a reamer configured to be driven or punched into the anatomy.

Figure 10:
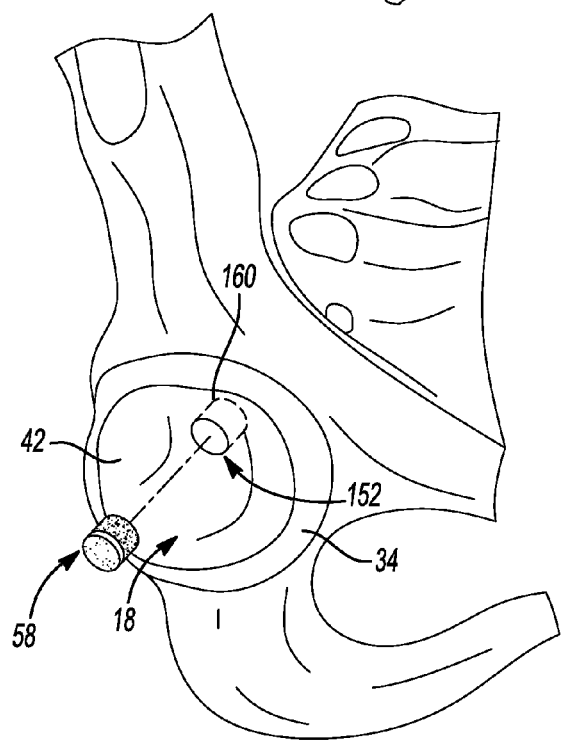
FIG. 10 is another perspective view of the cartilage plug harvesting technique associated with the acetabulum according to the present teachings.

With particular reference to FIGS. 6 and 9-10, preparation of a cartilage defect site 148 surrounding cartilage defect 62 in the femoral head and/or a cartilage defect site 152 surrounding the cartilage defect in the acetabulum 18 will now be described in greater detail. An exemplary coring reamer 156 or other suitable device can be used to ream a selected portion of the cartilage defect site 148 and/or 152 to prepare the sites for implantation of the harvested cartilage plug or plugs 58. Appropriate reamers 156 are generally known and need not be described in detail herein.

Reamer 156 can be used to ream a recipient socket in the form of a closed end bore 160 in the cartilage defect site 148 and/or 152 that substantially corresponds to a width of the harvested cartilage plug 58. Alternatively, the harvesting members 74, 104 can be provided with a range of sizes such that an appropriately sized harvesting member 74, 104 can be selected to harvest a cartilage plug 58 having a width that substantially corresponds to a width of the bore 160.

With particular reference to FIG. 6, the reamer 156 is shown being advanced toward cartilage defect site 148 and can ream the closed end bore 160, as generally shown with respect to another cartilage defect site 148 where the closed end bore has already been reamed. Similarly, and with particular reference to FIGS. 9 and 10, the reamer 156 is shown being advanced toward the cartilage defect site 152 in FIG. 9 and can be used to form the closed end bore 160 in defect site 152, as generally shown in FIG. 10. It should be appreciated that while only one cartilage defect site 152 has been shown with respect to acetabulum 18, the acetabulum 18 can include multiple cartilage defect sites 152 that can be treated according to the various methods of the present teachings.

The closed end bore 160 can include a shape and a width that corresponds to a shape and width of the harvested cartilage plug 58 such that the cartilage plug can be received in the reamed bore 160 in an interference-fit or press-fit relationship. Alternatively, the closed end bore can have a width and form such that the cartilage plug 58 can be received therein in a substantially slip-fit manner. The closed end bore can be reamed to a length or depth corresponding to the length or depth of the cartilage plug 58. It should be appreciated that the indentified cartilage defect sites 148 and/or 152 can be prepared before or after the cartilage plug or plugs 58 are harvested.

Figure 8:
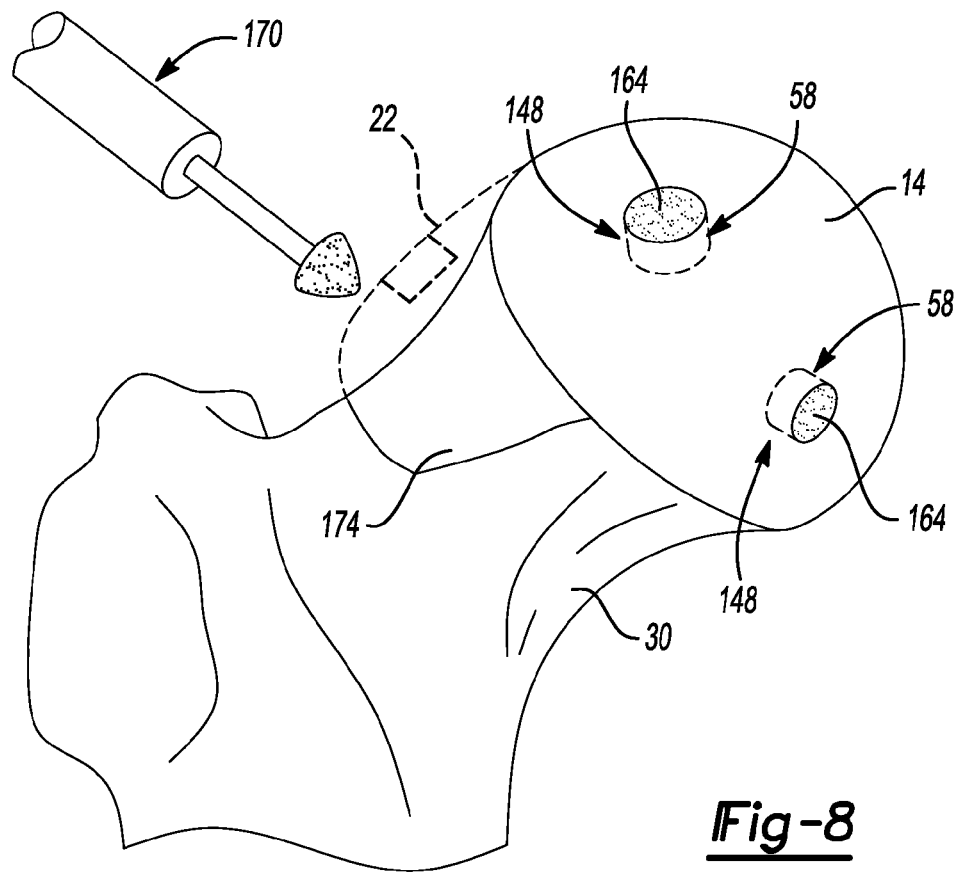
FIG. 8 is another perspective view of the cartilage plug harvesting technique associated with the femoral head according to the present teachings.
Figure 11:
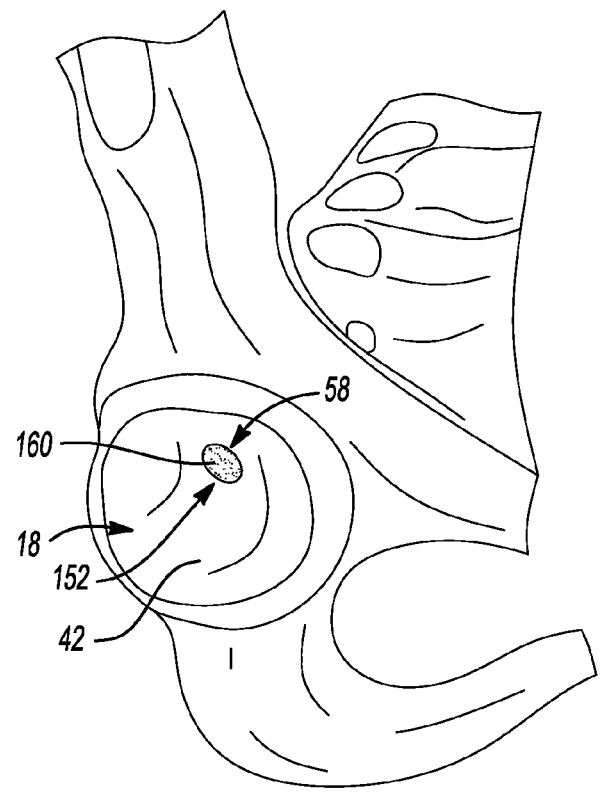
FIG. 11 is another perspective view of the cartilage plug harvesting technique associated with the acetabulum according to the present teachings.

Once the cartilage defect site 148 and/or 152 has been prepared, the harvested cartilage plug 58 can be implanted into the prepared site or sites, as generally shown in FIGS. 6 and 9 with respect to the femoral head 14 and FIGS. 10-11 with respect to the acetabulum. The cartilage plug 58 can be implanted in the press-fit configuration in bore 160 such that a top or articular surface 164 of the articular cartilage layer 59 is flush or substantially flush with a surface of the surrounding articular cartilage 42 or 54 of the femoral head 14 and/or acetabulum 18, as generally shown in FIG. 8 with regard to the femoral head 14 and FIG. 11 with regard to the acetabulum 18. Alternatively, the cartilage plug 58 can be implanted in the prepared bore 160 such that the articular surface 164 is slightly proud of or above the respective surrounding articular cartilage such that the cartilage plug presses into bore 160 over time to be flush or substantially flush with the surrounding articular cartilage. In addition, a fibrinogen glue or other biologic fixation agent can be used to enhance fixation of the cartilage plug 58 to the prepared bore 160 in the femoral head 14 and/or acetabulum 18.

With reference to FIGS. 6 and 8, a burr 170 or other appropriate tool can be used to remove the abnormal or excessive boney growth area 22 after the cartilage plug or plugs 58 have been harvested as described above. The burr 170 can be used to remove the boney growth area 22 so as to restore the sphericity of the femoral head 14, as well as remove any boney growth area 22 on the femoral neck 30 so as to alleviate or substantially reduce FAI that can be caused by the boney growth or build-up area 22 before removal. The femoral head and neck regions under the removed boney growth area 22 (shown in phantom in FIG. 8) can be resurfaced to restore the cortical bone to a smooth surface 174, as also shown in FIG. 8.

The technique described herein can allow for harvesting of cartilage plugs having an underlying bone layer from an area of abnormal excessive boney growth that would normally be milled away to correct for FAI. This can result in autograft material that can be used to correct for cartilage defects, sometimes caused by FAI. This technique can further reduce a need to harvest such cartilage plugs from other normal or good areas of the anatomy thereby reducing any potential pain, longer recovery time, etc., that may be associated therewith.

While one or more specific examples have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

What is claimed is:
1. A method for treating a cartilage defect, comprising:
   identifying an area of excessive boney growth on at least one of a femoral head and a femoral neck of a patient, the excessive boney growth area being covered with articular cartilage;
   determining whether the area of excessive boney growth is suitable for harvesting;
   harvesting a portion of the articular cartilage from the identified area of excessive boney growth;
   identifying an area of cartilage damage in an acetabulum of the patient; and implanting the harvested portion of the articular cartilage into the identified area of cartilage damage in the acetabulum.

2. The method of claim 1, wherein harvesting a portion of the identified articular cartilage includes harvesting a cartilage plug from the excessive boney growth area, the cartilage plug including an articular cartilage layer and an underlying bone layer.

3. The method of claim 2, wherein harvesting a cartilage plug from the excessive boney growth area includes harvesting the cartilage plug from only the excessive boney growth area.

4. The method of claim 2, further comprising determining a size of the identified area of cartilage damage in the acetabulum; and
selecting a harvesting instrument having a size sufficient to harvest the cartilage plug with a size equal to or greater than the determined size of the identified area of cartilage damage in the acetabulum;
wherein harvesting a cartilage plug includes driving the harvesting instrument into the boney growth area to harvest the cartilage plug, the cartilage plug being received in an inner cannula of the harvesting instrument.

5. The method of claim 4, wherein harvesting the cartilage plug includes harvesting the cartilage plug such that the harvested cartilage plug includes a width greater than a width of the closed end bore such that the harvested cartilage plug is implanted into the closed end bore in an interference fit configuration.

6. The method of claim 2, further comprising preparing the identified area of cartilage damage in the acetabulum to receive the harvested cartilage plug, said preparing including:
selecting a reaming instrument having a cutting size equal to or larger than the size of the area of cartilage damage;
aligning the reaming instrument with the area of cartilage damage; and
reaming a closed end bore through the area of cartilage damage and into the underlying bone;
wherein said closed end bore includes a width having a dimension configured to receive the cartilage plug in an interference fit.

7. The method of claim 6, wherein implanting the harvested portion of the articular cartilage includes implanting the harvested cartilage plug into the prepared closed end bore such that an articular surface of the articular cartilage layer of the harvested plug is flush with or proud of the surrounding articular cartilage of the acetabulum.

8. The method of claim 6, wherein harvesting a cartilage plug includes harvesting a cartilage plug having a selected length from a first end defined by an articular surface of the articular cartilage layer to an opposite second end defined by the underlying bone layer; and
wherein reaming a closed end bore includes reaming the closed end bore to a length substantially equal to the length of the harvested cartilage plug.

9. The method of claim 2, wherein harvesting a cartilage plug from the excessive boney growth area includes harvesting a plurality of separate cartilage plugs from the excessive boney growth area; and
wherein implanting the harvested portion of the articular cartilage includes implanting at least one of the harvested plurality of cartilage plugs into the identified area of cartilage damage in the acetabulum.

10. The method of claim 9, further comprising determining a size of a plurality of identified areas of articular cartilage damage, including a width and depth thereof;
wherein identifying an area of excessive boney growth further includes determining an amount of the identified excessive boney growth to be removed to reshape the at least one of the femoral head and femoral neck to substantially reduce femoro-acetabular impingement and mimic a normal shape of the at least one of the femoral head and femoral neck; and
wherein harvesting a plurality of separate cartilage plugs from the excessive boney growth area includes harvesting a plurality of cartilage plugs having different widths and depths, and selecting an area of the excessive boney growth to harvest each respective cartilage plug of the plurality of cartilage plugs to maximize an amount of the plurality of cartilage plugs that can be harvested from only the determined amount of excessive boney growth to be removed.

11. The method of claim 9, further comprising:
identifying an area of cartilage damage in an articulation area of the femoral head;
preparing the identified area of cartilage damage in the femoral head for receipt of one of the plurality or harvested cartilage plugs; and
implanting one of the plurality of harvested cartilage plugs into the prepared area of cartilage damage in the femoral head.

12. The method of claim 2, wherein the harvested cartilage plug includes a cylindrical shape or a conical shape having a width at an articular surface of the articular cartilage layer greater than a width of an opposite surface of the underlying bone layer.

13. The method of claim 1, further comprising removing the remaining excessive boney growth on the at least one of the femoral head and femoral neck to a shape of at least one of a normal femoral head and femoral neck after harvesting a portion of the articular cartilage from the identified area of excessive boney growth.

14. The method of claim 1, wherein the area of excessive boney growth would normally be milled away to correct for femoro-acetabular impingement.

15. A method for treating a cartilage defect, comprising:
identifying an area of excessive boney growth on at least a portion of one of a femoral head and a femoral neck of a patient, the excessive boney growth area being covered with articular cartilage;
determining whether the area of excessive boney growth is suitable for harvesting;
harvesting at least one cartilage plug from only the identified area of excessive boney growth, the at least one cartilage plug including an articular cartilage layer and an underlying bone layer, wherein the area of excessive boney growth would normally be milled away to correct for femoro-acetabular impingement;
identifying a cartilage defect site having an area of cartilage damage in at least one of the acetabulum and the femoral head of the patient;
preparing the identified cartilage defect site for receipt of the at least one harvested cartilage plug, the preparation including forming a closed end bore through the respective area of cartilage damage, the closed end bore having a width greater than a determined width of the area of cartilage damage;
implanting the at least one harvested cartilage plug into the formed closed end bore of the prepared defect site such that the implanted cartilage plug is received in the closed end bore in an interference fit configuration; and removing remaining excessive honey growth from the at least one of the femoral head and femoral neck after harvesting the at least one cartilage plug from the excessive honey growth.

16. The method of claim 15, wherein implanting the at least one cartilage plug further includes implanting the at least one cartilage plug in a prepared cartilage defect site of the acetabulum.

17. The method of claim 15, wherein harvesting at least one cartilage plug from only the identified area of excessive boney growth includes:
   selecting a harvesting instrument defining an inner cannula and a first end configured to engage the anatomy, the inner cannula having a width greater than a width of the closed end bore such that the harvested core plug can be implanted into the closed end bore in the interference fit configuration; and
   driving the first end of the harvesting instrument into the identified boney growth area to harvest the cartilage plug, the cartilage plug being received in the inner cannula.

18. The method of claim 15, wherein implanting the at least one harvested cartilage plug includes implanting the at least one harvested cartilage plug into the closed end bore of the prepared cartilage defect site in the acetabulum such that an articular surface of the articular cartilage layer of the at least one harvested plug is proud of the surrounding articular cartilage of the acetabulum.

19. A method for treating a cartilage defect, comprising:
   identifying an area of abnormal excessive boney growth on at least a portion of one of a femoral head and a femoral neck of a patient, the excessive boney growth area causing femoro-acetabular impingement and being covered with articular cartilage;
   inspecting the area of excessive boney growth for damage to the articular cartilage and determining whether the area of excessive honey growth is suitable for harvesting;
   determining a size of the excessive honey growth to be removed to substantially reduce the femoro-acetabular impingement and mimic a normal shape of the at least one of the femoral head and femoral neck;
   identifying a plurality of cartilage defect sites each having an area of cartilage damage in one of the acetabulum and the femoral head of the patient;
   determining a size, including a width and depth, of each of the plurality of identified cartilage defect sites;
   identifying specific areas of the determined size of the excessive honey growth to be removed for harvesting cartilage plugs, the specific areas identified being selected to maximize an amount of different sized cartilage plugs that can be harvested therefrom;
   harvesting a plurality of cartilage plugs from only the identified specific areas of excessive honey growth that is to be removed, the plurality of cartilage plugs each including an articular cartilage layer and an underlying bone layer, wherein the area of excessive boney growth would normally be milled away to correct for the femoro-acetabular impingement;
   preparing the identified plurality of cartilage defect sites for receipt of the plurality of harvested cartilage plugs, the preparation including forming a closed end bore through each of the respective areas of cartilage damage;
   implanting the plurality of harvested cartilage plugs into the corresponding formed closed end bores of the prepared plurality of cartilage defect sites such that each implanted cartilage plug is received in a respective closed end bore in an interference fit configuration; and
   removing remaining excessive boney growth from the at least one of the femoral head and femoral neck after harvesting the plurality of cartilage plugs from the excessive boney growth to mimic the normal shape of the at least one of the femoral head and femoral neck.

* * * * *

UNITED STATES PATENT AND TRADEMARK OFFICE
CERTIFICATE OF CORRECTION

| | | |
|---|---|---|
| PATENT NO. | : 8,641,718 B2 | Page 1 of 1 |
| APPLICATION NO. | : 12/907610 | |
| DATED | : February 4, 2014 | |
| INVENTOR(S) | : Jason D. Meridew | |

It is certified that error appears in the above-identified patent and that said Letters Patent is hereby corrected as shown below:

On The Title Page, item (56) References Cited, Other Publications, Column 2, line 14, Delete "Reconstrction,"" and insert --Reconstruction,"--.

In The Specification
Column 5, Line 62, Delete "indentified" and insert --identified--.

In the Claims
Column 6, Line 60, In Claim 1, delete "honey" and insert --boney--.
Column 7, Line 11, In Claim 2, delete "honey" and insert --boney--.
Column 7, Line 6, In Claim 3, delete "honey" and insert --boney--.
Column 8, Line 3, In Claim 10, delete "honey" and insert --boney--.
Column 8, Line 11, In Claim 10, delete "honey" and insert --boney--.
Column 8, Line 38, In Claim 14, delete "honey" and insert --boney--.
Column 8, Line 43, In Claim 15, delete "honey" and insert --boney--.
Column 8, Line 51, In Claim 15, delete "honey" and insert --boney--.
Column 9, Line 1, In Claim 15, delete "honey" and insert --boney--.
Column 9, Line 4, In Claim 15, delete "honey" and insert --boney--.
Column 9, Line 37, In Claim 19, delete "honey" and insert --boney--.
Column 10, Line 1, In Claim 19, delete "honey" and insert --boney--.
Column 10, Line 11, In Claim 19, delete "honey" and insert --boney--.
Column 10, Line 16, In Claim 19, delete "honey" and insert --boney--.

Signed and Sealed this
Twenty-eighth Day of April, 2015

Michelle K. Lee
*Director of the United States Patent and Trademark Office*